United States Patent [19]

Alexander et al.

[11] Patent Number: 5,780,478
[45] Date of Patent: Jul. 14, 1998

[54] TETRA-SUBSTITUTED PHENYL DERIVATIVES

[75] Inventors: Rikki Peter Alexander, High Wycombe; Graham John Warrellow, Northwood, both of United Kingdom

[73] Assignee: Celltech Therapeutics, Limited, Slough, United Kingdom

[21] Appl. No.: 493,264

[22] Filed: Jun. 21, 1995

[30] Foreign Application Priority Data

Jun. 22, 1994 [GB] United Kingdom ............... 9412571

[51] Int. Cl.$^6$ .......... A61K 31/44; C07D 213/30; C07D 213/34; C07D 213/64
[52] U.S. Cl. ............ 514/277; 514/357; 546/301; 546/302; 546/334; 546/300
[58] Field of Search ............... 546/301, 334, 546/300, 302; 514/277, 357

[56] References Cited

U.S. PATENT DOCUMENTS

| | | | |
|---|---|---|---|
| 4,012,795 | 3/1977 | Schmiechen et al. | 514/424 |
| 4,015,017 | 3/1977 | Gazave | 514/687 |
| 4,153,713 | 5/1979 | Huth et al. | 514/423 |
| 4,193,926 | 3/1980 | Schmiechen et al. | 548/517 |
| 4,303,649 | 12/1981 | Jones | 514/8 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,550,137 | 8/1996 | Beeley et al. | 514/354 |
| 5,580,888 | 12/1996 | Warrellow et al. | 514/332 |
| 5,608,070 | 3/1997 | Alexander et al. | 546/270 |

FOREIGN PATENT DOCUMENTS

| | | |
|---|---|---|
| 2501443 | 7/1975 | Denmark . |
| 0233461A2 | 8/1987 | European Pat. Off. . |
| 0295210A1 | 12/1988 | European Pat. Off. . |
| 0337943A2 | 10/1989 | European Pat. Off. . |
| 0470805 | 2/1990 | European Pat. Off. . |
| 0393500 | 10/1990 | European Pat. Off. . |
| 0490823 | 6/1992 | European Pat. Off. . |
| 0497564A1 | 8/1992 | European Pat. Off. . |
| 0511865 | 11/1992 | European Pat. Off. . |
| 0537742 | 4/1993 | European Pat. Off. . |
| 0564409A1 | 10/1993 | European Pat. Off. . |
| 2545356A1 | 11/1984 | France . |
| 3-77872 | 4/1991 | Japan . |
| 3-77923 | 4/1991 | Japan . |
| 1588639 | 4/1981 | Ukraine . |
| 87/06576 | 11/1987 | WIPO . |
| 91/15451 | 10/1991 | WIPO . |
| 91/16892 | 11/1991 | WIPO . |
| 92/00968 | 1/1992 | WIPO . |
| 92/06085 | 4/1992 | WIPO . |
| 92/06963 | 4/1992 | WIPO . |
| 92/07567 | 5/1992 | WIPO . |
| 92/12961 | 8/1992 | WIPO . |
| 92/19594 | 11/1992 | WIPO . |

(List continued on next page.)

OTHER PUBLICATIONS

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Daves, G.D. et al., "Pyrimidines. XIII. 2–and 6–Substituted 4–Pyrimidinecarboxylic Acids", *J Of Hev. Chem.*, 1964, 1, 130–133.

Dietl, F. et al., "Chinone von Benzo–und Dibenzokroneneth-ern", *Synthesis*, 1985, 626–631.

(List continued on next page.)

*Primary Examiner*—Alan L. Rotman
*Attorney, Agent, or Firm*—Woodcock Washburn Kurtz Mackiewicz & Norris LLP

[57] ABSTRACT

Compounds of general formula (1):

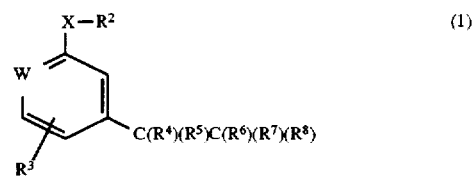

are described
wherein =W— is (1) =C(Y)— where Y is a halogen atom, or an alkyl, or —X$^a$R$^1$ group where X$^a$ is —O—, —S(O)$_m$— [where m is zero or an integer of value 1 or 2], or —N(R$^a$)— [where R$^a$ is a hydrogen atom or an optionally substituted alkyl group] and R$^1$ is a hydrogen atom or an optionally substituted alkyl group or, (2) =N—; X is as described above for X$^a$ or is a chain —CR=C(R$^b$)— or [—CH(R)]$_q$—CH(R$^b$)— where R is a hydrogen or a fluorine atom or a methyl group, R$^b$ is as described below for R$^2$ and q is zero or the integer 1; R$^2$ is (1) an optionally substituted alkyl, alkenyl, cycloalkyl or cycloalkenyl group when X is —O—, —S(O)$_m$— or —N(R$^a$)—; atoms or groups; R$^3$ is an atom or group R$^{13}$;

R$^4$ is a hydrogen atom or is as defined for R$^6$; R$^5$ is a hydrogen or a fluorine atom; R$^6$ is a group —(CH$_2$)$_n$Ar where Ar is an optionally and R$^8$, which may be the same or different, is a hydrogen or a fluorine atom, or an optionally substituted straight or branched alkyl group; and the salts, solvates, prodrugs, hydrates and N-oxides thereof.

Compounds according to the invention are phosphodiesterase type IV inhibitors and are useful in the prophylaxis and treatment of disease such as asthma where an unwanted inflammatory response or muscular spasm is present.

18 Claims, No Drawings

FOREIGN PATENT DOCUMENTS

| | | |
|---|---|---|
| 92/19602 | 11/1992 | WIPO . |
| 93/19748 | 10/1993 | WIPO . |
| 94/02465 | 2/1994 | WIPO . |
| 94/12461 | 6/1994 | WIPO . |
| 94/14742 | 7/1994 | WIPO . |
| 94/20446 | 9/1994 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |

OTHER PUBLICATIONS

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Hanks, S.K. et al., "the eukaryotic protein kinase superfamily: kinase (catalytic) domain structure and classification", *FASEB J.*, 1995, 9, 576–596.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2) , 123–132.

Newton, A.C., "Protein Kinase C: Structure, Function, Regulation", *J. Biol. Chem.*, 1995, 270(48) , 28495–28498.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocylic Chem.*, 1994, 31, 1311–1315.

Sá,nchez, H.I. et al., "Formal Total Synthesis of β–Pipitzol", *Tetrahedron*, 1985, 41(12), 2355–2359.

Sakakibara, K. et al., "Preparation of N–pyridyl–4–(benzyloxy) benzamides as Cardiotonics", *Chem. Abstr.* 1988, 108, No. 131583p.

Tsutsumi, K. et al., "Preparation of (Dialkoxyphosphinoylmethyl) benzamides as Antihyperlipidemics", *Chem. Abstr.* 1990, 113, No. 6599a.

Ashton, "Selective Type IV Phosphodiesterase Inhibitors as Antiasthmatic Agents. The Synthesis and Biological Activities of 3–(Cyclopentyloxy) –4–methoxybenzamides and Analogues" J. Med. Chem. 37: pp. 1696–1703 (1994).

Beavo & Reifsnyder, "Primary Sequence of Cyclic Nucleotide Phosphodiesterase Isozymes and the Design of Selective Inhibitors" TIPS 11: pp. 150–155 (1990).

Buu–Hoi, N.P. et al., "Bromination of Some 1,2,2–Triarylethylenes" *J. of Organic Chemistry*, 23 : pp. 1261–1263 (Sep. 1958).

Buu–Hoi et al., "New Method for the Synthesis of ω,ω–Diarylacetophenones Aminated in the Aromatic Nucleus. Polynitration of Triarylethylenes" Chemical Abstracts 61: 16006h (1964).

Chemical Abstracts. Registry Handbook –Number Section. Printed Issues Columbus US *compounds with registry numbers 95992–21–5; 95971–60–1; 90053–37–5; 82668–18 –6; 8–80395–25–1; 49610–49–3.

El–Wakil et al., "Study of the Proton Magnetic Resonance of Methoxytamoxifen Towards Ortho–Substitution" Chemical Abstracts 116: 255248t (1992).

Hirose et al., "Styrene Derivatives and Electrophotographic Photoreceptor Containing Them" Chemical Abstracts 118: 136183z (1993).

Lisle, H. et al., "IL–5–Induced Eosinophilia in the Rat Pleural Cavity: The Effect of Dexamethasone and Indomethacin", *Br. J. Pharmacol.* 108, 230: (1993).

Livi et al., "Cloning and Expression of cDNA for a Human Low–$K_m$ 3 Rolipram–Sensitive Cyclic AMP Phosphodiesterase", *Molecular and Cellular Biol.* 10: pp. 2678–2686 (1990).

Ishikura, M. et al., "An Efficient Synthesis of 3–Heteroarylpyridines via Diethyl–(3–pyridyl) –borane" Synthesis. pp. 936–938 (1984).

Manhas et al., "Heterocyclic Compounds XII. Quinazoline Derivatives as Potential Antifertility Agents(1)" J. Heterocyclic Chem. 16: pp. 711–715 (1979).

Meyers, A.I. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 39: p. 2787–2793 (1974).

Mezheritskaya, "Synthesis and Properties of Carboxonium Het=Erocyclic Systems. VII. Synthesis and Properties of 2–Benzyl–Substituted 1,3–Dioxalanium Salts" Chem. Abs. 93: 95160j p. 635 (1980).

Mitsunobu, O., "The Use of Diethyl Azodicarboxylate and Triphenylphosphine in Synthesis and Transformation of Natural Products" Synthesis 1: pp. 1–28 (1981).

Nicholson et al.,"Differential Modulation of Tissue Function and Therapeutic Potential of Selective Inhibitors of Cyclic Nucleotide Phosphodiesterase Isoenzymes" TIPS 12: pp. 19–27 (1991).

O'Connor et al., "Voltammetry and Controlled Potential Oxidation of 3,4–Dimethoxypropenylbenzene at a Rotating Platinum Electrode in Unbuffered Acetonitrile and in Acetonitrile–Pyridine Solution" Chemical Abstracts 60 (8) #10203.4 (Apr. 13, 1964).

Porter et al., "Preparation of 6–phenyl–3–(5–tetrazolyl)pyridin–=2(H) –one Derivatives as Cyclic AMP–dependent Protein Kinase Agonists" Chem. Abstract 117(9) : 90296n (1992).

Ramalingam, Deshmukh and Sattur, "Synthesis and Pharmacology of 2,5–Disubstituted 1,3,4–Zxadiazoles" J. Indian Chem. Soc. v. 58(3) 269–271 (1981).

Reddy et al., "Inhibition of Breast Cancer Cell Growth in Vitro by a Tyrosine Kinase Inhibitor" Cancer Research 52: 3636–3641 (1992).

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" J. Med. Chem. 29: 1355–1362 (1986).

Seitz et al., "Fluorotamoxifen. A Caveat on the Generality of Electrophilic Destannylation" Chemical Abstracts 111: 57133k (1989).

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls" Tetrahedron Lett 28: 5093–5096 (1987).

Thompson, W.J. and Gaudino, J., "A General Synthesis of 5–Arylnicotinates" J. Org. Chem. 39: 5237–5243 (1984).

Yeadon et al., "Mechanisms Contributing to Ozone–Induced Bronchial Hyperreactivity in Guinea Pigs", *Pulmonary Pharm.* 1992, 5, 39.

Yoneda et al., "The Antiproliferative Effects of Tyrosine Kinase Inhibitors Tyrphostins on a Human Squamous Cell Carcinoma in Vitro and in Nude Mice" Cancer Research 51: 4430–4435 (1991).

Green and Wuts, "Protective Groups in Organic Synthesis", John Wiley & Sons, New York, 1981.

TETRA-SUBSTITUTED PHENYL DERIVATIVES

This invention relates to a novel series of tetra-substituted phenyl derivatives, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of tetra-substituted phenyl derivatives, members of which are potent inhibitors of PDE IV at concentrations at which they have little or no inhibitory action on other PDE isoenzymes. These compounds inhibit the human recombinant PDE IV enzyme and also elevate cAMP in isolated leukocytes. The compounds of the invention are therefore of use in medicine, especially in the prophylaxis and treatment of asthma.

Thus according to one aspect of the invention, we provide a compound of formula (1)

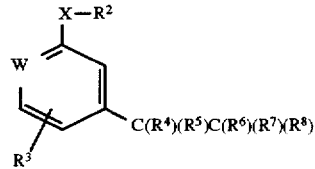

wherein
=W— is (1) =C(Y)— where Y is a halogen atom, or an alkyl, or —$X^a R^1$ group where $X^a$ is —O—, —S(O)$_m$— [where m is zero or an integer of value 1 or 2], or —N($R^a$)— [where $R^a$ is a hydrogen atom or an optionally substituted alkyl group] and $R^1$ is an optionally substituted alkyl group or, (2) =N—;

X is as described above for $X^a$ or is a chain —CR=C($R^b$)— or —[—CH(R)]$_q$—CH($R^b$)— where R is a hydrogen or a fluorine atom or a methyl group, $R^b$ is as described below for $R^2$ and q is zero or the integer 1;

$R^2$ is (1) an optionally substituted alkyl, alkenyl, cycloalkyl or cycloalkenyl group when X is —O—, —S(O)$_m$— or —N($R^a$)—; or when X is —CR=C($R^b$)— or —[—CH(R)]$_q$CH($R^b$)— is (2) a hydrogen atom, or an optionally substituted straight or branched alkyl, alkenyl or alkynyl, alkoxy, alkylthio, —CO$_2 R^9$ (where $R^9$ is a hydrogen atom or an optionally substituted alkyl, aryl or aralkyl group), —CONR$^{10}$R$^{11}$ (where $R^{10}$ and $R^{11}$ which may be the same or different is as described for $R^9$), —CSNR$^{10}$R$^{11}$, —CN or NO$_2$ group; or $R^2$ and $R^b$, together with the carbon atom to which they are both attached, are linked to form an optionally substituted cycloalkyl or cycloalkenyl group optionally containing one or more $X^a$ atoms or groups;

$R^3$ is an atom or group $R^{13}$ or —$L^1 R^{13}$ where $L^1$ is a linker group and $R^{13}$ is a halogen atom or an Alk$^1$ [where Alk$^1$ is an optionally substituted straight or branched $C_{1-6}$alkyl, $C_{2-6}$alkenyl or $C_{2-6}$alkynyl group optionally interrupted by one, two, or three —O—, or —S— atoms or —S(O)$_p$—, [where p is an integer 1 or 2], or —N($R^a$)— groups], or an amino (—NH$_2$), substituted amino, nitro, cyano, hydroxyl (—OH), substituted hydroxyl, cycloalkyl, cycloalkoxy, formyl [HC(O)—], carboxyl (—CO$_2$H), esterified carboxyl, thiol (—SH), substituted thiol, —C(O)Alk$^1$, —SO$_3$H, —SO$_2$Alk$^1$, —SO$_2$NH$_2$, —SO$_2$NHAlk$^1$, —SO$_2$N[Alk$^1$]$_2$, —SO$_2$NHAr [where Ar is as defined below for $R^6$], —SO$_2$N(Alk$^1$)Ar, —CONH$_2$, —CONHAlk$^1$, —CON[Alk$^1$]$_2$, —CONHAr, —CON(Alk$^1$)Ar, —NHSO$_2$H, —NAlk$^1$SO$_2$H, —NHSO$_2$Alk$^1$, —NAlk$^1$SO$_2$Alk$^1$, —N[SO$_2$Alk$^1$]$_2$, —N(Alk$^1$)SO$_2$N(Alk$^1$)Ar, —NHSO$_2$NH$_2$, —N(Alk$^1$)SO$_2$NH$_2$, —NHSO$_2$NHAlk$^1$, —N(Alk$^1$)SO$_2$NHAlk$^1$, —NHSO$_2$N[Alk$^1$]$_2$, —NAlk$^1$SO$_2$N[Alk$^1$]$_2$, —NHSO$_2$NHAr, —N(Alk$^1$)SO$_2$NHAr, —NHSO$_2$N(Alk$^1$)Ar, —N(Alk$^1$)SO$_2$N(Alk$^1$)Ar, —NHC(O)Alk$^1$, —N(Alk$^1$)C(O)Alk$^1$, —N[C(O)Alk$^1$]$_2$, —NHC(O)OAlk$^1$, —N(Alk$^1$)C(O)OAlk$^1$, —Ar, —Het [where Het is a $C_{5-7}$ heterocycloalkyl group], —CONHet$^1$ [where —NHet$^1$ is a $C_{5-7}$ cycloamino group optionally containing one or more —O— or —S— atoms or —N($R^a$)— groups], —SO$_2$NHet$^1$, —NHSO$_2$NHet$^1$, —CSAlk$^1$, —CSNH$_2$, —CSNHAlk$^1$, —CSN[Alk$^1$]$_2$, —CSNHAr, —CSN(Alk$^1$)Ar, —NHC(S)Alk$^1$, —N(Alk$^1$)C(S)Alk$^1$, —CSNHet$^1$ group, —N[C(S)Alk$^1$]$_2$, —N[C(O)Alk$^1$|SO$_2$Alk$^1$, —N[C(S)Alk$^1$|SO$_2$Alk$^1$, —NHC(O)NH$_2$, —NHC(O)NHAlk$^1$, —NHC(O)N[Alk$^1$]$_2$, —N(Alk$^1$)CONH$_2$, —N(Alk$^1$)C(O)NHAlk$^1$, —N(Alk$^1$)C(O)N[Alk$^1$]$_2$, —NHC(S)NH$_2$, —NHC(S)NHAlk$^1$, —NHC(S)N[Alk$^1$]$_2$, —N(Alk$^1$)CSNH$_2$, —N(Alk$^1$)C(S)NHAlk$^1$, or —N(Alk$^1$)C(S)N[Alk$^1$]$_2$, group;

$R^4$ is a hydrogen atom or is as defined for $R^6$;

$R^5$ is a hydrogen or a fluorine atom, or an OR$^c$ group where $R^c$ is a hydrogen atom or an optionally substituted straight or branched alkyl, alkenyl, alkoxyalkyl, alkanoyl, formyl, carboxamido, thiocarboxamido, cycloalkyl, or cycloalkenyl group;

$R^6$ is a group —(CH$_2$)$_n$Ar where Ar is an optionally substituted monocyclic or bicyclic aryl ring optionally interrupted by one or more heteroatoms —O—, —S— or —N— and n is zero or the integer 1, 2 or 3;

$R^7$ and $R^8$, which may be the same or different, is a hydrogen or a fluorine atom, or an optionally substituted straight or branched alkyl group; and the salts, solvates, prodrugs, hydrates and N-oxides thereof.

It will be appreciated that compounds of formula (1) may have one or more chiral centres depending on the nature of the groups X, R, $R^3$, $R^4$, $R^5$, $R^6$, and $R^7$. Where one or more chiral centres is present, enantiomers or diasteromers may exist, and the invention is to be understood to extend to all such enantiomers, diastereomers and mixtures thereof, including racemates.

Compounds of formula (1) where X is a chain —CR=C($R^b$)— may exist as geometric isomers depending on the nature of the groups R, $R^b$ and $R^2$, and the invention is to be understood to extend to all such isomers and mixtures thereof.

In the compounds of formula (1), when Y is a halogen atom it may be for example a fluorine, chlorine, bromine or iodine atom.

When =W— in the compounds of formula (1) is a group =C(Y)— where Y is a group —$X^a R^1$, $R^1$ may be, for example, an optionally substituted straight or branched alkyl group, for example, an optionally substituted $C_{1-6}$alkyl group, such as a methyl, ethyl, n-propyl or i-propyl group. Optional substitutents which may be present on $R^1$ groups include one or more halogen atoms, e.g. fluorine, or chlorine atoms. Particular $R^1$ groups include for example —$CH_2F$, —$CH_2Cl$, —$CHF_2$, —$CHCl_2$, —$CF_3$ or —$CCl_3$ groups.

When =W— in compounds of formula (1) is a group =C(Y)— where Y is $X^a R^1$ in which $X^a$ is a —N($R^a$)— group, $X^a$ may be a —NH—, —$NCH_2$— or —$NC_2H_4$- group.

Alkyl groups represented by $R^1$, $R^2$, $R^6$, $R^7$, or $R^8$ in compounds of formula (1) include optionally substituted straight or branched $C_{1-6}$ alkyl groups, e.g. $C_{1-3}$ alkyl groups such as methyl or ethyl groups. Optional substituents on these groups include one, two or three substituents selected from halogen atoms, e.g. fluorine, chlorine, bromine or iodine atoms, or hydroxyl or $C_{1-6}$ alkoxy e.g. $C_{1-3}$ alkoxy such as methoxy or ethoxy groups.

Alkenyl groups represented by $R^2$, or $R^c$ in compounds of formula (1) include optionally substituted straight or branched $C_{2-6}$alkenyl groups such as ethenyl, propen-1-yl and 2-methylpropen-1-yl. Optional substituents include those described above in relation to the alkyl groups represented by $R^2$.

Alkynyl groups represented by $R^2$, or $R^b$ in compounds of formula (1) include optionally substituted straight or branched $C_{2-6}$alkynyl groups optionally interrupted by one or more $X^a$ atoms or groups. Particular examples include ethynyl and propyn-1-yl groups. Optional substituents include those described above in relation to alkyl groups represented by $R^2$.

When $R^2$, or $R^b$ or $R^2$ and $R^b$, together with the carbon atom to which they are both attached, are an optionally substituted cycloalkyl or cycloalkenyl group the group may be for example a $C_{3-8}$cycloalkyl group such as a cyclobutyl, cyclopentyl or cyclohexyl group or a $C_{3-8}$ cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

When the group =W— in compounds of formula (1) is a group =C(Y)— in which Y is a halogen atom Y may be for example a fluorine, chlorine, bromine or iodine atom.

Particular examples of —$(CH_2)_n$Ar groups represented by $R^4$ and/or $R^6$ include —Ar, —$CH_2$Ar, —$(CH_2)_2$Ar or —$(CH_2)_3$Ar groups.

Monocyclic or bicyclic aryl groups represented by the group Ar in compounds of formula (1) include for example $C_{6-12}$ optionally substituted aryl groups, for example optionally substituted phenyl, 1-or 2-naphthyl, indenyl or isoindenyl groups.

When the monocyclic or bicyclic aryl group Ar contains one or more heteroatoms it may be for example a $C_{1-9}$ optionally substituted heteroaryl group containing for example one, two, three or four heteroatoms selected from oxygen, sulphur or nitrogen atoms. In general, Ar heteroaryl groups may be for example monocyclic or bicyclic heteroaryl groups. Monocyclic heteroaryl groups include for example five- or six-membered heteroaryl groups containing one, two, three or four heteroatoms selected from oxygen or sulphur atoms or a group —N($R^a$)—.

Examples of heteroaryl groups represented by Ar include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

The heteroaryl group represented by Ar may be attached to the remainder of the molecule of formula (1) through any ring carbon or heteroatom as appropriate. Thus, for example, when the group Ar is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group.

When in compounds of formula (1) the Ar group is a nitrogen-containing heterocycle it may be possible to form quaternary salts, for example N-alkyl quaternary salts and the invention is to be understood to extend to such salts. Thus for example when the group Ar is a pyridyl group, pyridinium salts may be formed, for example N-alkylpyridinium salts such as N-methylpyridinium.

The aryl or heteroaryl groups represented by Ar in compounds of formula (1) may each optionally be substituted by one, two, three or more $R^{13}$ substituents.

When $R^{13}$ in compounds of formula (1) is a substituted amino group it may be a group —NH[$Alk^1(R^{13a})_z$] [where z is zero or an integer 1, 2 or 3 and $R^{13a}$ is as defined above for $R^{13}$ but is not a substituted amino, a substituted hydroxyl or a substituted thiol group] or a group —N[$Alk^1(R^{13a})_z$]$_2$ wherein each —$Alk^1(R^{13a})_z$ group is the same or different.

When $R^{13}$ is a cycloalkoxy group it may be for example a $C_{5-7}$cycloalkoxy group such as a cyclopentyloxy or cyclohexyloxy group.

When $R^{13}$ is a substituted hydroxyl or substituted thiol group it may be a group —O$Alk^1(R^{13a})_z$ or —S$Alk^1(R^{13a})_z$ respectively, where $Alk^1$, $R^{13a}$ and z are as just defined.

Esterified carboxyl groups represented by the group $R^{13}$ include groups of formula —$CO_2 Alk^2$ wherein $Alk^2$ is a straight or branched, optionally substituted $C_{1-8}$alkyl group such as a methyl, ethyl, n-propyl, i-propyl, n-butyl, i-butyl, s-butyl or t-butyl group; a $C_{6-12}arylC_{1-8}alkyl$ group such as an optionally substituted benzyl, phenylethyl, phenylpropyl, 1-naphthylmethyl or 2-naphthylmethyl group; a $C_{6-12}aryl$ group such as an optionally substituted phenyl, 1-naphthyl or 2-naphthyl group; a $C_{6-12}aryloxyC_{1-8}alkyl$ group such as an optionally substituted phenyloxymethyl, phenyloxyethyl, 1-naphthyloxymethyl, or 2-naphthyloxymethyl group; an optionally substituted $C_{1-8}alkanoyloxyC_{1-8}alkyl$ group, such as a pivaloyloxymethyl, propionyloxyethyl or propionyloxypropyl group; or a $C_{6-12}aroyloxyC_{1-8}alkyl$ group such as an optionally substituted benzoyloxyethyl or benzoyloxypropyl group. Optional substituents present on the $Alk^2$ group include $R^{13}$ substituents described above.

Particular examples of —Het groups represented by the group $R^{13}$ include optionally substituted pyrrolyl, e.g. 2H-pyrrolyl, pyrrolinyl, e.g. 2- or 3-pyrrolinyl, pyrrolidinyl, 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, 3H-pyrrolyl, 2H-imidazolyl, dithiolyl, e.g. 1, 2- or 1,3-dithiolyl, oxathiolyl, e.g. 3H-1-2 or 1,3-oxathiolyl, 5H-1,2,5-oxathiozolyl, 1,3-dioxinyl, oxazinyl, e.g. 2H-1,3-, 6H-1,3-, 6H-1,2-, 1,4-2H-1,2- or 4H-1,4-oxazinyl, 1,2,5-oxathiazinyl, isoxazinyl, e.g. -o- or p-isoxazinyl, oxathiazinyl, e.g. 1,2,5-, 1,2,6-oxathiazinyl, 1,3,5,2-oxadiazinyl, or 1,2,4-diazepinyl groups. Optional substituents which may be present on such groups include those substituents discussed above in relation to the alkyl groups represented by $R^1$, $R^2$, $R^6$, $R^7$ or $R^8$.

Examples of the group $Alk^1$ in compounds of formula (1) include methyl, ethyl, n-propyl, i-propyl, n-butyl, i-butyl, s-butyl, t-butyl, ethenyl, 2-propenyl, 2-butenyl, 3-butenyl, ethynyl, 2-propynyl, 2-butynyl or 3-butynyl groups optionally interrupted by one, two or three —O— or —S— atoms or —S(O)—, —S(O)$_2$— or —N(R$^a$)— groups.

Particularly useful atoms or groups represented by $R^{13}$ include fluorine, chlorine, bromine or iodine atoms, or $C_{1-6}alkyl$, e.g. methyl or ethyl, $C_{1-6}$ alkylamino, e.g. methylamino or ethylamino, $C_{1-6}$ hydroxyalkyl, e.g. hydroxymethyl or hydroxyethyl, $C_{1-6}alkylthiol$ e.g. methylthiol or ethylthiol, $C_{1-6}alkoxy$, e.g. methoxy or ethoxy, $C_{5-7}$ cycloalkyl, e.g. cyclopentyl, $C_{5-7}$ cycloalkoxy, e.g. cyclopentyloxy, halo$C_{1-6}$alkyl, e.g. trifluoromethyl, $C_{1-6}$ alkylamino, e.g. methylamino or ethylamino, amino (—NH$_2$), amino$C_{1-6}$ alkyl, e.g. aminomethyl or aminoethyl, $C_{1-6}dialkylamino$, e.g. dimethylamino or diethylamino, nitro, cyano, hydroxyl (—OH), formyl |HC(O)—|, carboxyl (—CO$_2$H), —CO$_2$Alk$^2$ [where Alk$^2$ is as defined above], $C_{1-6}alkanoyl$ e.g. acetyl, thiol (—SH), thio$C_{1-6}alkyl$, e.g. thiomethyl or thioethyl, optionally substituted phenyl or naphthyl (where the optional substituents are selected from one or more atoms or groups $R^{13}$ or $L^1R^{13}$), a group —Het as just described above, sulphonyl (—SO$_3$H), $C_{1-6}$ alkylsulphonyl, e.g. methylsulphonyl, aminosulphonyl (—SO$_2$NH$_2$), $C_{1-6}$ alkylaminosulphonyl, e.g. methylaminosulphonyl or ethylaminosulphonyl, $C_{1-6}dialkylaminosulphonyl$, e.g. dimethylaminosulphonyl or diethylaminosulphonyl, phenylaminosulphonyl, carboxamido (—CONH$_2$), $C_{1-6}alkylaminocarbonyl$, e.g. methylaminocarbonyl or ethylaminocarbonyl, $C_{1-6}$ dialkylaminocarbonyl, e.g. dimethylaminocarbonyl or diethylaminocarbonyl, phenylaminocarbonyl, sulphonylamino (—NHSO$_2$H), $C_{1-6}$ alkylsulphonylamino, e.g. methylsulphonylamino or ethylsulphonylamino, $C_{1-6}dialkylsulphonylamino$, e.g. dimethylsulphonylamino or diethylsulphonylamino, aminosulphonylamino (—NHSO$_2$NH$_2$), $C_{1-6}alkylaminosulphonylamino$, e.g. methylaminosulphonylamino or ethylaminosulphonylamino, $C_{1-6}dialkylaminosulphonylamino$, e.g. dimethylaminosulphonylamino or diethylaminosulphonylamino, phenylaminosulphonylamino, $C_{1-6}alkanoylamino$, e.g. acetylamino, $C_{1-6}alkanoylamino$, $C_{1-6}alkyl$, e.g. acetylaminomethyl or $C_{1-6}alkoxycarbonylamino$, e.g. methoxycarbonylamino, ethoxycarbonylamino, or t-butoxycarbonylamino, thiocarboxamido (—CSNH$_2$), $C_{1-6}$ alkylaminothiocarbonyl, e.g. methylaminothiocarbonyl or ethylaminothiocarbonyl, $C_{1-6}dialkylaminothiocarbonyl$, e.g. dimethylaminothiocarbonyl or diethylaminothiocarbonyl, phenylaminothiocarbonyl, aminocarbonylamino, $C_{1-6}alkylaminocarbonylamino$, e.g. methylaminocarbonylamino or ethylaminocarbonylamino, $C_{1-6}dialkylaminocarbonylamino$, e.g. dimethylaminocarbonylamino or diethylaminocarbonylamino, aminothiocarbonylamino, $C_{1-6}alkylaminothiocarbonylamino$, e.g. methylaminothiocarbonylamino or ethylaminothiocarbonylamino, $C_{1-6}$ dialkylaminothiocarbonylamino, e.g. dimethylaminothiocarbonylamino, or diethylaminothiocarbonylamino, aminocarbonyl$C_{1-6}alkylamino$, e.g. aminocarbonylmethylamino or aminocarbonylethylamino, aminothiocarbonyl$C_{1-6}alkylamino$ e.g. aminothiocarbonylmethylamino or aminothiocarbonylethylamino, formylamino$C_{1-6}$ alkylsulphonylamino, e.g. formylaminomethylsulphonylamino or formylaminoethylsulphonylamino, thioformylamino$C_{1-6}alkylsulphonylamino$, e.g. thioformylaminomethylsulphonylamino or thioformylethylsulphonylamino, $C_{1-6}acylaminosulphonylamino$, e.g. acetylaminosulphonylamino, $C_{1-6}thioacylaminosulphonylamino$, e.g. thioacetylaminosulphonylamino groups.

In the compounds of formula (1), when $R^3$ is a $L^1R^{13}$ group the linker group $L^1$ may be any divalent linking group. Particular examples of $L^1$ groups include groups of formula —(Alk$^a$)$_r$(X$^a$)$_s$(Alk$^b$)$_t$— where Alk$^a$ and Alk$^b$ is each an optionally substituted straight or branched $C_{1-6}alkylene$, $C_{2-6}alkenylene$ or $C_{2-6}alkynylene$ chain optionally interrupted by one or more, e.g. one, two or three heteroatoms or carbocyclic or heteroatom-containing groups, $X^a$ is an —O— or —S— atom or a —S(O)—, —S(O)$_2$— or —N(R$^b$)— group, r is zero or the integer 1, t is zero or the integer 1 and s is zero or the integer 1, provided that when one of r, s, or t is zero at least one of the remainder is the integer 1.

The heteroatoms which may interrupt the Alk$^a$ or Alk$^b$ chains include for example —O— or —S— atoms. Carbocyclic groups include for example cycloalkyl, e.g. cyclopentyl or cyclohexyl, or cycloalkenyl e.g. cyclopentenyl or cyclohexenyl, groups. Particular heteroatom-containing groups which may interrupt Alk$^a$ or Alk$^b$ include oxygen-, sulphur- or nitrogen-containing groups such as —S(O)—, —S(O)$_2$—, —N(R$^b$)—, —C(O)—, —C(S)—, —C(NR$^b$)—, —CON(R$^b$)—, —CSN(R$^b$)—, —N(R$^b$)CO—, —N(R$^b$) CS—, —SON(R$^b$)—, —SO$_2$N(R$^b$)—, —N(R$^b$)SO—, —N(R$^b$)SO$_2$—, —N(R$^b$)SO$_2$N(R$^b$)—, —N(R$^b$)SON(R$^b$)—, —N(R$^b$)CON(R$^b$)—, or N(R$^b$)CSN(R$^b$)— groups. It will be appreciated that when the chains Alk$^a$ or Alk$^b$ are interrupted by two or more heteroatoms, carbocyclic or heteroatom-containing groups, such atoms or groups may be adjacent to one another, for example to form a group —N(R$^b$)—C(NR$^b$) —N(R$^b$)— or —O—CONH—.

Optional substituents which may be present on $Alk^a$ or $Alk^b$ chains include those described above in relation to the group $R^1$ when it is an alkyl group.

In the group —$L^1R^{13}$ particular examples of $Alk^a$ or $Alk^b$ when present include optionally substituted methylene, ethylene, propylene, butylene, ethenylene, 2-propenylene, 2-butenylene, 3-butenylene, ethynylene, 2-propynylene, 2-butynylene or 3-butynylene chains, optionally interrupted by one, two or three heteroatoms, carbocyclic or heteroatom-containing groups as described above.

Particular groups represented by —$L^1R^{13}$ include for example —$CH_2Ar$, —$(CH_2)_2Ar$, —$CH$=$CHAr$, —$(CH_2)_3Ar$, —$CH_2CH$=$CHAr$, —$OCH_2Ar$, —$CH_2OAr$, —$CH_2OCH_2Ar$, —$CH_2N(R^a)Ar$ or —$CH_2N(R^a)CH_2Ar$ groups.

The group $R^3$ in compounds of formula (1) may in general be attached to the remainder of the molecule through a carbon atom adjacent to the group —$C(R^4)(R^5)C(R^6)(R^7)(R^8)$ or the group W.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In compounds of formula (1), the group =W— is preferably a =C(Y)— group in which Y is an —$OR^1$ group, especially where $R^1$ is an optionally substituted ethyl group, or an optionally substituted methyl group. Especially useful substituents which may be present on $R^1$ groups include one, two or three fluorine or chlorine atoms.

The group X in compounds of formula (1) is preferably —O—.

Particularly useful groups of compounds of formula (1) have the formula (2)

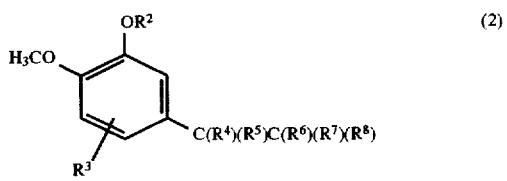

(2)

where $R^2$ is an optionally substituted cycloalkyl group; $R^3$, $R^4$, $R^5$, $R^6$, $R^7$ and $R^8$ are as defined for formula (1); and the salts, solvates, hydrates, prodrugs and N-oxides thereof.

In the compounds of formulae (1) and (2), $R^2$ is preferably an optionally substituted methyl or cyclopentyl group. In particular $R^2$ is a cyclopentyl group.

In the compounds of formulae (1) and (2) $R^4$ is preferably a hydrogen atom or an —Ar or —$CH_2Ar$ group, where Ar is an optionally substituted aryl or heteroaryl group, particularly a phenyl or nitrogen containing heteroaryl group such as a pyridyl group. In general however in compounds of formulae (1) and (2) $R^4$ is especially a hydrogen atom.

The groups $R^5$, $R^7$ and $R^8$ in compounds of formulae (1) and (2) is each preferably a fluorine atom or especially a hydrogen atom.

In the compounds of formulae (1) and (2) the group $R^6$ is preferably an —Ar group, especially a nitrogen containing monocyclic heteroaryl group.

Particularly useful groups of this type are optionally substituted pyridyl groups, particularly optionally substituted 4-pyridyl groups.

In the compounds of formulae (1) and (2) $R^3$ is preferably a halogen atom or an optionally substituted $C_{1-6}$alkyl, $C_{2-6}$alkenyl, $C_{2-6}$alkynyl, $C_{6-12}$ mono- or bicyclic aryl, $arC_{1-3}$alkyl or $arC_{1-3}$alkenyl, or $C_{1-9}$ mono- or bicyclic heteroaryl or heteroar$C_{1-3}$alkyl group. Optional substituents which may be present on these groups include, for alkyl, alkenyl or alkynyl groups, those substituents described above in relation to the group $R^1$, and for aryl, aralkyl, heteroaryl or heteroaralkyl groups, $R^{13}$ substituents as described above.

Particular examples of aryl or aralkyl groups include optionally substituted phenyl, naphthyl, phen$C_{1-3}$alkyl or naphthyl$C_{1-3}$alkyl groups. Examples of heteroaryl or heteroaralkyl groups include optionally substituted pyridyl or pyridyl$C_{1-3}$alkyl groups.

Particular examples of $R^3$ in the compounds of formulae (1) and (2) include bromine, chlorine or iodine atoms or, methyl, ethyl, ethenyl 2-propenyl, ethynyl, 2-propynyl, phenyl, naphthyl, benzyl, phenylethyl, phenylethenyl, phenylpropen-1-yl, phenylpropen-2-yl, 2-, 3- or 4-pyridyl, 2-, 3- or 4- pyridylmethyl, or 2-, 3- or 4-pyridylethyl, each of said phenyl or pyridyl groups being optionally substituted by one or more $R^{13}$ substituents.

The group $R^3$ may in particular be positioned on one of the two ring carbon atoms between the group W and the group —$C(R^4)(R^5)C(R^6)(R^7)(R^8)$ either adjacent to the group W or adjacent to the group —$C(R^4)(R^5)C(R^6)(R^7)(R^8)$.

Particularly useful compounds according to the invention are:

4-[2-(5-Cyclopentyloxy-2-iodo-4-methoxyphenyl)ethyl] pyridine;

4-[2-(5-Cyclopentyloxy-4-methoxy-2-phenyl)ethyl] pyridine;

4-{2-[5-Cyclopentyloxy-4-methoxy-2-(2-phenylethenyl) phenyl]ethyl}pyridine;

4-{2-[5-Cyclopentyloxy-4-methoxy-2-(2-phenylethyl) phenyl]ethyl} pyridine;

4-{2-[5-Cyclopentyloxy-4-methoxy-2-(1-naphthyl)phenyl] ethyl} pyridine;

4-{2-[5-Cyclopentyloxy-4-methoxy-2-(2-naphthyl)phenyl] ethyl} pyridine;

4-{2-[5-Cyclopentyloxy-4-methoxy-2-(3-pyridyl)phenyl] ethyl}pyridine;

or each isomer and enantiomer, and/or the salts, hydrates, solvates, prodrugs and N-oxides thereof.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention have also been found to reduce gastric acid secretion and therefore can be used to treat conditions associated with hypersecretion.

Compounds of the invention suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention ameliorate these symptoms with a consequent enhancement of quality of life.

Compounds of the invention also elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds according to the invention may be prepared by the following processes. The symbols W, $R^2$, $R^3$, $R^4$, $R^5$, $R^6$, $R^7$, $R^8$ and X, when used in the formulae below are to be understood to represent those groups described above in relation to formula (1) unless otherwise indicated. In the reactions described below it may be necessary to protect reactive functional groups, for example hydroxy, amino, thio, carboxy or aldehyde groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981.] It may be that deprotection will form the last step in the synthesis of compounds of formula (1).

Thus according to a further aspect of the invention, a compound of formula (1) where $R^3$ is a group —$L^1R^{13}$ may be prepared by a cross-coupling reaction of compound of formula (3)

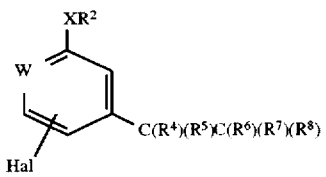

where Hal is an iodine or bromine atom with a coupling reagent.

The reaction may be carried out in the presence of a metal catalyst, such as a metal complex catalyst, for example a palladium complex e.g. dichloro-[1,4-bis(diphenylphosphino)ferrocene]palladium, tetrakis(triphenylphosphine)palladium, or palladium (II) acetate, or a nickel complex such as dichloro-[1,3-bis(diphenylphosphino)propane] nickel.

The coupling reagents include organometallic reagents, such as organo magnesium reagents $R^{13}L^1MgX$, where X is a halogen atom, such as a chlorine or bromine atom, organozinc reagents $R^{13}L^1ZnX$; boronic acid derivatives, for example $R^{13}L^1B(OH)_2$ in the presence of a base, such as a carbonate e.g. sodium carbonate; or an olefin reagent for example $R^{13}L^1CH=CH_2$ in the presence of a phosphine, e.g. tri-0-tolylphosphine and a base such as triethylamine.

The reaction may take place in a solvent, for example an ether, such as diethylether or a cyclic ether, e.g. tetrahydrofuran or dioxane, or a nitrile, e.g. acetonitrile, at a temperature varied from room temperature to an elevated temperature, e.g. 140° C.

The coupling reagents are either known compounds or may be prepared using reagents and conditions similar to those used for the preparation of the known compounds.

It is to be understood that compounds of formula (3) are compounds of formula (1) in which $R^3$ is a halogen atom. Therefore, in a further aspect of the invention compounds of formula (1) wherein $R^3$ is a halogen atom may be prepared by halogenation of a compound of formula (4)

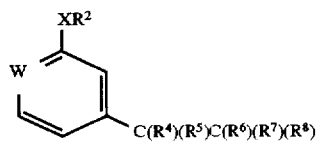

This reaction is particularly suitable for preparing compounds in which $R^3$ is a chlorine, bromine or iodine atom. Thus for example bromination and chlorination may be achieved by using bromine or chlorine in the presence of a catalyst, such as a Lewis acid, e.g. $AlBr_3$, $AlCl_3$, or $FeCl_3$ respectively or an organic acid, e.g. acetic acid where necessary in a solvent for example a halogenated hydrocarbon, e.g. dichloromethane.

Iodination may be carried out by the use of iodine in the presence of an oxidising agent, such as $HNO_3$, $HIO_3$, or peracetic acid, or salts, such as copper salts, antimony salts e.g. $SbCl_5$ or sulphonates, e.g. silver trifluoromethanesulphonate, where necessary in a solvent such as a halogenated hydrocarbon, e.g. dichloromethane.

Intermediates of formula (4) where $R^5$ is a hydroxyl group may be prepared by reaction of a compound of formula (5)

with (a) an organometallic reagent $R^6R^7R^8CM$ where M is a metal atom, such as lithium, or a Grignard reagent $R^6R^7R^8MgHal$, where Hal is a halogen atom, e.g. a bromine atom, or (b) a compound $R^6R^7R^8CHal$, where Hal is a halogen atom, such as a bromine atom, using a base, such as t-butyllithium.

Intermediates of formula (4), where $R^5$ is a fluorine atom may be prepared by reacting an intermediate of formula (4), where $R^5$ is a hydroxyl group, with a fluorinating reagent, such as diethylaminosulphur trifluoride (DAST), in a solvent, for example a chlorinated solvent, e.g. dichloromethane, at a low temperature, e.g. around 0° C.

Ketones of formula (5) may be prepared by oxidation of a corresponding alcohol of formula (6)

using an oxidising agent such as manganese dioxide in a solvent such a dichloromethane at ambient temperature.

Alcohols of formula (6) may be prepared by reaction of an aldehyde of formula (7)

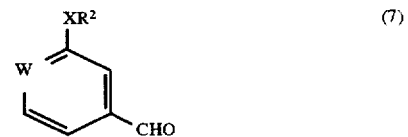

with an organometallic compound, such as organolithium compound $R^4Li$, or a Grignard reagent $R^4MgBr$, in a solvent, such as tetrahydrofuran, at a low temperature, e.g. around –50° C. to 0° C.

Aldehydes of formula (7) where =W— is =C(Y)— may be prepared by alkylation of a corresponding compound of formula (8):

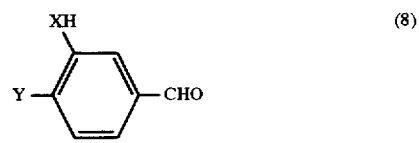

using a compound $R^2Hal$ [where Hal is as previously defined] using the reagents and conditions described hereinafter for the alkylation of intermediates of formula (15).

Intermediates of formula (8) are either known compounds or may be prepared from known starting materials by methods analogous to those used for the preparation of the known compounds.

Intermediates of formula (7) wherein =W— is =N— may be prepared from an intermediate of formula (9)

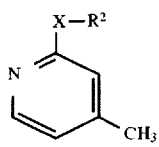
(9)

by successive oxidation and reduction reactions.

For example a first oxidation of intermediate (9) by SeO$_2$ or potassium permanganate gives the carboxylic acid derivative. This in turn may be reduced by a reducing agent, for example lithium aluminium hydride to afford the corresponding alcohol, which upon oxidation with manganese dioxide gives the desired intermediate (7).

Intermediates of formula (9) may be prepared by reacting a halide of formula (10)

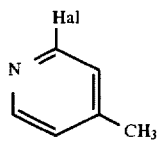
(10)

where Hal is a halogen atom, e.g. a bromine, chlorine or iodine atom with a compound RXH, where X is —O—, —S— or —NH— in the presence of a base.

Bases used in this reaction include hydrides, such as sodium hydride, or organometallic bases, such as butillithium in a solvent, such as an amide, for example dimethylformamide at a temperature from room temperature to above, e.g. around 80° C.

Intermediates of formula (10) may be prepared by reacting the commercially available amine of formula (11)

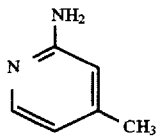
(11)

with nitrous acid (made in situ by reacting sodium nitrite with an acid, for example sulphuric acid or hydrobromic acid) to produce the diazonium salt. This in turn may be reacted with a haloacid, e.g. hydrobromic, hydrochloride or hydriodic acid if necessary in the presence of the corresponding copper (1) halide for example CuBr or CuI, or halogen, e.g. bromine, chlorine or iodine.

Alternatively ketones of formula (5) may be prepared by reaction of a halide of formula (12)

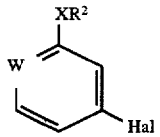
(12)

[where Hal is a halogen atom such as bromine or chlorine atom] by halogen metal exchange with a base such as n-butyllithium followed by reaction with a nitrile R$^4$CN, an acid chloride R$^4$COCl or an ester R$^4$CO$_2$Alk (where Alk is an alkyl group, e.g. a methyl group), in a solvent such as tetrahydrofuran at a low temperature, e.g. around −70° C., and subsequent treatment with an acid such as hydrochloric acid at e.g. −20° C. to ambient temperature.

Halides of formula (12) may be prepared by alkylation of a compound of formula (13):

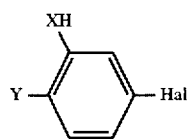
(13)

using the reagents and conditions discussed below in relation to the alkylation of intermediates of formula (15).

Halides of formula (13) where X is —O— may be prepared by oxidation of an aldehyde of formula (14):

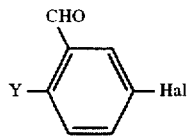
(14)

using an oxidising agent such as 3-chloroperoxybenzoic acid in a halogenated hydrocarbon such as chloroform at a temperature from around 0° C. to room temperature.

Aldehydes of formula (14) and halides of formula (13) where X is —S— or —N(R$^8$)— are either known compounds or may be prepared from known starting materials by methods analogous to those used for the preparation of the known compounds.

Intermediates of formula (5) where X is —O—, —S— or —N(R$^a$)— may also be prepared by alkylation of a compound of formula (15)

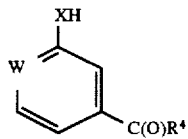
(15)

using a reagent R$^2$L, where L is a leaving group.

Leaving groups represented by L include halogen atoms such as iodine, chlorine or bromine atoms, or sulphonyloxy groups such as aryl-sulphonyloxy groups, e.g. p-toluenesulphonyloxy.

The alkylation reaction may be carried out in the presence of a base, such as a carbonate, e.g. caesium or potassium carbonate, an alkoxide, e.g. potassium t.butoxide, or a hydride, e.g. sodium hydride, in a dipolar aprotic solvent such as an amide, e.g. a substituted amide such as dimethylformamide, or an ether, e.g. a cyclic ether such as tetrahydrofuran, at ambient temperature or above, e.g. around 40° C. to 50° C.

Intermediates of formula (15) are known compounds or may be prepared in a manner similar to the preparation of the known compounds.

In yet another process according to the invention, compounds of formula (1) where R$^8$ and R$^5$ is each a hydrogen atom may be prepared by hydrogenation of a compound of formula (16)

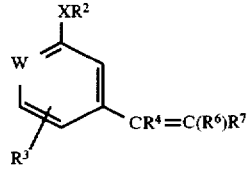
(16)

The hydrogenation may be performed using for example hydrogen in the presence of a catalyst. Suitable catalysts include metals such as platinum or palladium, optionally supported on an inert carrier such as carbon or calcium carbonate; nickel e.g. Raney Nickel, or rhodium. The reaction may be performed in a suitable solvent, for example an alcohol such as methanol or ethanol, an ether such as tetrahydrofuran or dioxane, or an ester such as ethyl acetate, optionally in the presence of a base, for example a tertiary organic base such as triethylamine, at for example ambient temperature.

Alternatively, the reaction may be accomplished by transfer hydrogenation using an organic hydrogen donor and a transfer agent. Suitable hydrogen donors include for example acids, such as formic acid, formates, e.g. ammonium formates, alcohols, such as benzyl alcohol or ethylene glycol, hydrazine, and cycloalkenes such as cyclohexene or cyclohexadiene. The transfer agent may be for example a transition metal, for example palladium or platinum, optionally supported on an inert carrier as discussed above, nickel e.g. Raney nickel, ruthenium, e.g. tris (triphenylphosphine) ruthenium chloride or copper. The reaction may generally be performed at ambient or elevated temperature, optionally in the presence of a solvent, for example an alcohol such as ethanol or an acid such as acetic acid.

Intermediate alkenes of formula (16) may be obtained by reaction of a corresponding aldehyde of formula (5) [where $R^4$ is a hydrogen atom] using an olefination agent and the reagents and conditions similar to those described below for the production of a compound of formula (1) from an intermediate of formula (19).

In another process according to the invention, a compound of formula (1) where X is —O—, —S— or —N($R^a$)— may be prepared by alkylation of a compound of formula (17)

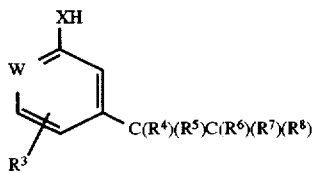

(17)

using a reagent $R^2L$, as described above for the production of a compound of formula (5) from a compound of formula (15).

Intermediates of formula (17) may be obtained from the corresponding protected compounds of formula (18)

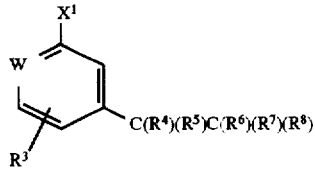

(18)

wherein $X^1$ is a protected hydroxy, thio, amino or aldehyde group using conventional deprotection procedures [see Green, T. W. ibid]. Thus for example where $X^1$ is a t-butyldimethylsilyloxy group, the required hydroxyl group may be obtained by treatment of the protected intermediate with tetra-butylammonium fluoride. In another example where $X^1$ is a dioxanyl group, the required aldehyde group may be obtained by acid hydrolysis of the protected intermediate with trifluoroacetic acid or p-toluene sulphonic acid, in the presence of a solvent, e.g. acetone, or a mixture of solvents, e.g. chloroform and water.

The protected intermediates of formula (18) may be prepared in an analogous manner to the compounds of formula (1) using the reactions described herein and appropriately protected intermediates.

In a further aspect of the invention, compounds of general formula (1) where X is a chain —C(R)=C($R^b$)—, in which R is a hydrogen atom or a methyl group, may be prepared by coupling a compound of formula (19)

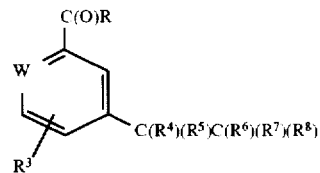

(19)

where R is as defined above with an olefination agent

Particular examples of olefination agents include phosphonium salts such as compounds $(R^b)(R^2)CHP(D)_3Hal$ where Hal is a halogen atom, such as a bromine atom, and D is an optionally substituted alkyl, e.g. methyl, or aryl, especially phenyl, group; phosphoranes $(R^b)(R^2)C=P(D)_3$; phosphonates $(DO)_2P(O)CH(R^b)(R^2)$; or silane derivatives, for example compounds of formula $(D)_3SiC(R^5)(R^6)$, e.g. trialkylsilanes such as $(CH_3)_3SiC(R^b)(R^2)$.

Bases for use in the above reaction include organometallic bases, for example, an organolithium compound such as an alkyllithium e.g. n-butyllithium, a hydride, such as sodium or potassium hydride or an alkoxide, such as a sodium alkoxide, e.g. sodium methoxide.

The reaction may be performed in a suitable solvent, for example a polar aprotic solvent, such as an alkyl sulphoxide, e.g. methyl sulphoxide, an amide such as N,N-dimethylformamide or hexamethylphosphorous triamide; a non-polar solvent, such as an ether, e.g. tetrahydrofuran or diethyl ether or an aromatic solvent such as benzene, toluene or xylene; or a polar protic solvent, such as an alcohol, for example ethanol. Preferably the reaction is carried out at a low temperature, for example from around −78° C. to around room temperature.

The olefination agents used in this reaction are either known compounds or may be prepared from known starting materials using reagents and conditions similar to those used to prepare the known compounds. For example, a phosphorane may be prepared in situ by reaction of a phosphonium salt with a base of the type described above. In another example, a phosphonate may be prepared by reacting a halide $(R^b)(R^2)CHHal$ with a phosphite $(DO)_3P$, as described in the Arbuzov reaction. Silane derivatives may be prepared by reaction of a halosilane $(D)_3SiHal$ with a base, such as lithium diisopropylamide, in a solvent, such as an ether, for example a cyclic ether, e.g. tetrahydrofuran, at low temperature, e.g. −10° C.

According to a further aspect of the invention compounds of formula (1) where X is a group —C(R)=CH($R^b$) and $R^2$ is an optionally substituted alkyl, alkenyl or alkynyl group may also be prepared by reaction of an intermediate of formula (19) with an organometallic reagent, for example as described above in connection with the preparation of intermediates of formula (4), followed by dehydration of the corresponding alcohol. The dehydration may be performed using an acid, for example an organic acid such as p-toluene sulphonic acid or trifluoroacetic acid, in the presence of a base, such as an amine, e.g. triethylamine.

Intermediates of formula (19) may be prepared by deprotecting an intermediate of formula (20)

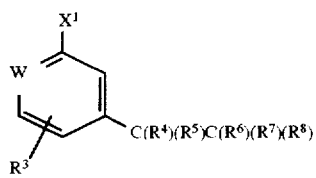

where $X^1$ is an aldehyde or ketone protecting group.

Intermediates of formula (20) may be prepared by reaction of a compound of formula (21)

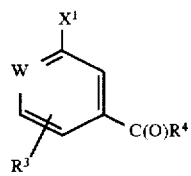

with an organometallic reagent or a halide in an analogous manner to the preparation of intermediates of formula (4) from intermediates of formula (5)

Intermediates of formula (21) may be prepared by oxidation of an alcohol of formula (22)

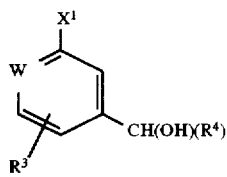

using an oxidising agent, such as manganese (IV) oxide, in a solvent, such as dichloromethane, at room temperature.

Intermediates of formula (22) may be prepared by reaction of a halide of formula (23)

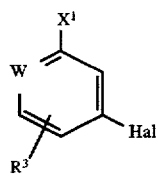

with an aldehyde $R^4$CHO, in the presence of a base, such as n-butyllithium, in a solvent, e.g. tetrahydrofuran, at a temperature from around $-70°$ C. to room temperature.

Intermediates of formula (23) may be prepared by protecting an aldehyde of formula (24)

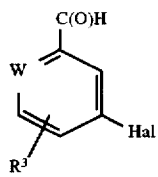

using the reagents and conditions described herein above.

Intermediates of formula (24) are either known compounds or may be prepared in a similar manner to the known compounds.

In another aspect of the invention, a compound a formula (1) in which =W— is a =C($X^aR^1$)— group in which $X^a$ is —O— may be prepared by alkylating an intermediate of formula (25)

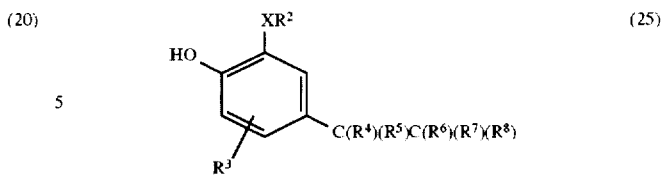

using a reagent $R^1$ L where L is a leaving group as described above.

The reaction may be performed using the reagents and conditions described above for the production of a compound of formula (5) from a compound of formula (15).

Intermediates of formula (25) where $R^3$ is propen-2-yl may be prepared in a Claisen rearrangement by heating an allylic aryl ether of formula (26)

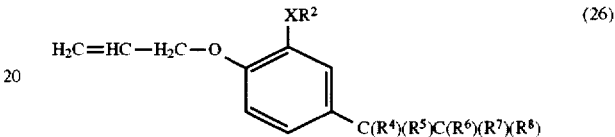

at elevated temperature.

Intermediates of formula (23) may be prepared by reacting an intermediate of formula (4) where W is a =C(OCH$_3$)— group with a thiol reagent, such as propanethiol, in the presence of a base, such as a hydride, e.g. sodium or potassium hydride, or an amide, e.g. sodium bis (trimethylsilyl)amide. The reaction may be performed in a solvent, such as dimethylformamide at an elevated temperature, e.g. the reflux temperature.

Intermediates of formula (25) may also be prepared by deprotecting a compound of formula (26)

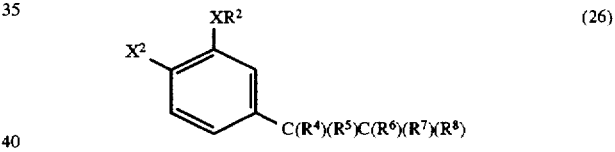

where $X^2$ is a protected hydroxyl group, e.g. methoxy, using iodotrimethylsilane in chloroform.

Intermediates of formula (24) may be prepared using similar protected reagents and conditions to those used for the preparation of intermediates of formula (4).

Compounds of formula (1) may also be prepared by interconversion of other compounds of formula (1). These reactions will generally involve the group $R^{13}$, whether present as the group $R^3$ or as a substituent on a group Ar in $R^4$ or $R^6$. Thus, in one example of an interconversion process a compound of formula (1) which contains a —CH$_2$NH$_2$ substituent may be prepared by reduction of a corresponding compound of formula (1) which contains a nitrile group, using for example a complex metal hydride such as lithium aluminium hydride in a solvent such as an ether e.g. diethylether.

In a further example, a compound of formula (1) with an alkanoylamino or alkanoylaminoalkyl substituent may be prepared by acylation of a corresponding compound of formula (1) containing a —NH$_2$ or alkylamino group by reaction with an acyl halide in the presence of a base, such as a tertiary amine e.g. triethylamine in a solvent such as dichloromethane.

Compounds of formula (1) where X is a chain [—CH(R)]$_q$—CH($R^b$)— may be prepared by hydrogenation of a compound of formula (1) where X is a chain —C(R)=C($R^b$)— using the reagents and conditions described above for the production of a compound of formula (1) from an intermediate of formula (13).

In yet another example of an interconversion process, compounds of formula (1) containing an ester [$CO_2Alk^2$], e.g. an ethanoate, may be prepared by esterification of a corresponding compound of formula (1) containing a carboxylic acid, using an acid halide, such as an acid chloride, e.g. acetyl chloride, in an alcohol, such as ethanol, at an elevated temperature, such as the reflux temperature.

Compounds of formula (1) containing a carboxylic acid may be prepared from the corresponding compound of formula (1) containing a formyl group, by oxidation with an oxidising agent, e.g. potassium permanganate, in a solvent, such as an alcohol, e.g. tert-butanol, at ambient temperature.

In a further interconversion reaction, compounds of formula (1) which contain an aminoalkyl group, such as dimethylaminomethyl, may be prepared by reductive amination of a corresponding compound of formula (1) which contains a formyl group, using an amine, e.g. dimethylamine, in the presence of a reducing agent, e.g. sodium cyanoborohydride, if necessary in the presence of a catalyst, e.g. ethanolic HCl, in a solvent, such as an alcohol, e.g. methanol, at ambient temperature.

In another example of an interconversion reaction a compound of formula (1) which contains a formyl group, may be reduced to the corresponding alcohol, using a reducing agent, e.g. sodium borohydride, in a solvent, such as an alcohol, e.g. ethanol, at a temperature from around 0° C. to ambient temperature. The resulting alcohol may then be converted to a corresponding alkoxy derivative, e.g. methoxymethyl, by reaction with an alkyl halide or alkyl sulphonate using the methods and reagents described above for the alkylation of intermediates of formula (9).

In a further example of an interconversion process compounds of formula (1) which contain a carboxamido (—$CONHAlk^1$) or an aminocarbonyl (—$NHCOAlk^1$) group may be prepared by reaction of the corresponding compound containing a —$CO_2H$ or a —$NH_2$ group respectively by reaction with a carbamate, such as i-butyl chloroformate or ethyl chloroformate, in the presence of a base, such as an amine, e.g. triethylamine or N-methylmorpholine, in a solvent, such as dichloromethane, or a mixture of solvents, e.g. tetrahydrofuran and dimethylformamide, at a temperature from around −20° C. to room temperature.

In a still further interconversion reaction, compounds of formula (1) which contain a —$NHCONHAlk^1$ group may be prepared by reacting a corresponding compound of formula (1) which contains an amino (—$NH_2$) group, with an isocyanate, e.g. ethyl isocyanate, in a solvent, e.g. dichloromethane, at ambient temperature.

In another example of an interconversion process, compounds of formula (1) wherein $R^7$ is an alkyl group, may be prepared by interconversion of a compound of formula (1) where $R^7$ is a hydrogen atom by reaction with a compound $R^7L$, where L is a leaving group, for example a halogen atom, such as chlorine, in the presence of a base, for example lithium diisopropylamide, in a solvent such as tetrahydrofuran, at low temperature, such as 0° C.

Compounds of formula (1) wherein $R^5$ is an $OR^c$ group where $R^c$ is an alkyl, alkoxyalkyl, formyl or alkanoyl group, may be prepared in another example of an interconversion process by reaction of a compound of formula (1) where $R^5$ is a —OH group with a compound $R^cL$ (where $R^c$ is as just defined and L is a leaving group as described above), in a solvent, such as dichloromethane or tetrahydrofuran in the presence of a base, for example triethylamine or potassium tert-butoxide, at room temperature.

In a further interconversion process compounds of formula (1) wherein $R^c$ is a carboxamido (—$CONHAlk^1$) or a thiocarboxamido (—$CSNHAlk^1$) group, may be prepared by reaction of a compound of formula (1) wherein $R^5$ is a hydroxyl group with an isocyanate $Alk^1$ NCO or an isothiocyanate $Alk^1NCS$, in a solvent, for example chloroform, in the presence of a base, for example diisopropylethylamine, at ambient temperature. The isocyanate $Alk^1NCO$ and isothiocyanate $Alk^1NCS$ are known compounds or may be prepared in a conventional manner.

In a further example, a compound of formula (1) wherein $R^c$ is a $CON[Alk^1]_2$ group may be prepared by reaction of a compound of formula (1) wherein $R^c$ is a $CONHAlk^1$ group with a reagent $Alk^1L$ (where L is a leaving group as described above) in the presence of a base, for example sodium hydride, in a solvent, such as tetrahydrofuran, at low temperature, for example 0° C.

In another example, an isothiocyanate of formula (1) where $R^c$ is —$CSN[Alk^1]_2$ may be prepared by reacting a compound of formula (1) wherein $R^c$ is a —$CON[Alk^1]_2$ group with a thiation reagent, such as Lawesson's Reagent, in an anhydrous solvent, for example toluene, at elevated temperature, such as the reflux temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid or base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral acid or base. Suitable chiral acids include, for example, tartaric acid and other tartrates such as dibenzoyl tartrates and ditoluoyl tartrates, sulphonates such as camphor sulphonates, mandelic acid and other mandelates and phosphates such as 1,1'-binaphthalene-2,2'-diyl hydrogen phosphate. The diastereomers may then be separated by any convenient means, for example by crystallisation and the desired enantiomer recovered, e.g. by treatment with an acid or base in the instance where the diastereomer is a salt.

In another resolution process a racemate of formula (1) may be separated using chiral High Performance Liquid Chromatography.

Alternatively, if desired a particular enantiomer may be obtained by using an appropriate chiral intermediate in one of the processes described above.

The following examples illustrate the invention. The following abbreviations are used: DMF—dimethylformamide; THF—tetrahydrofuran; DME—dimethoxyethane; EtOAc—ethyl acetate; $Et_2O$—diethylether; $Et_3N$—triethylamine; BuLi—butyllithium; LDA—lithium diisopropylamide; EtOH—ethanol; $CHCl_3$—chloroform; $CH_2Cl_2$—dichloromethane; MeOH—methanol; RT—room temperature.

INTERMEDIATE 1
3-Cyclopentyloxy-4-methoxybenzaldehyde

The title compound was prepared as described for Intermediate 9 in International Patent Specification No. WO 94/14742.

INTERMEDIATE 2
(±)-4-|2-(3-Cyclopentyloxy-4-methoxyphenyl)-2-hydroxyethyl|pyridine The title compound was prepared as described in Example 2b) in International Patent Specification No. WO 94/20446.

INTERMEDIATE 3
(E)-4-|2-(3-Cyclopentyloxy-4-methoxyphenyl)ethenyl| pyridine

The title compound was prepared as described for Intermediate 5c) in International Patent Specification No. WO 94/20446.

INTERMEDIATE 4
4-|2-(3-Cyclopentyloxy-4-methoxyphenyl)ethyl|pyridine

The title compound was prepared as described in Example 3f) in International Patent Specification No. WO 94/20446.

INTERMEDIATE 5
(R)-(+)-4-|2-(3-Hydroxy-4-methoxyphenyl)-2-phenylethyl| pyridine To a stirred solution of NaH (60% dispersion in mineral oil) (0.483 g, 12.075 mmol) in DMF under nitrogen at RT was added propanethiol (1.09 ml, 12.07 mmol) and the mixture stirred for 30 min. A solution of (R)-(+)-4-|2-(3-cyclopentyloxy-4-methoxyphenyl)-2-phenylethyl|pyridine (made as described in WO 94/14742) (1.8 g, 4.83 mmol) in DMF was added, the mixture heated to reflux for 5 h, allowed to cool (the reaction was followed by tic) and concentrated in vacuo. The residue was taken up in $CH_2Cl_2$ and washed with aqueous $NaHCO_3$ solution. The aqueous phase was extracted with $CH_2Cl_2$, the combined organic phase dried ($MgSO_4$), filtered and concentrated in vacuo. The residue was subjected to chromatography ($SiO_2$; $Et_2O$) then recrystallised (i-propylether) to give the title compound (6.00 g) as a white solid. m.p. 158°–159° C. (Found C, 79.37; H, 6.96; N, 3.66. $C_{24}H_{25}O_2N$ requires C, 80.19; H, 7.01; N, 3.90%). $δ_H$ (CDCl$_3$) 1.5–1.9 (8H, m, (CH$_2$)$_4$), 3.39 (2H, dd, J 8, 1 Hz, CH$_2$ pyridine), 4.12 (1H, t, J 8 Hz, CHCH$_2$), 4.62 (1H, m, OCH), 5.52 (1H, br s, OH), 6.57 (1H, m, C$_6$H$_3$), 6.6–6.7 (1H, m, C$_6$H$_3$), 6.75–6.8 (1H, m, C$_6$H$_3$), 6.91 (2H, d, J 6, Hz, H$_3$, H$_5$ pyridine), 7.1–7.3 (5H, m, C$_6$H$_5$), and 8.38 (2H, d, J 6 Hz, H$_2$, H$_6$ pyridine).

INTERMEDIATE 6
4-|2-(R)-(3-Cyclopentyloxy-4-prop-2-enyloxyphenyl)-2-phenylethyl|-pyridine hyrochloride To a stirred solution of Intermediate 5 (2.031 g, 5.66 mmol) in THF (60 ml) and DMF (20 ml) at RT, under nitrogen, was added potassium t-butoxide (0.8 g, 6.77 mmol). After 20 min, allyl bromide (0.56 ml, 6.47 mmol) was added, the mixture stirred at RT for 20 min then quenched with water and extracted with EtOAc. The combined organic phase was dried (MgSO$_4$), filtered and concentrated in vacuo to give the title compound free base (2.2 g) as a yellow gum.

A small amount of the free base was treated with etheral HCl to give the title compound as an off-white solid (Found C, 71.18; H, 6.58; N, 2.93. $C_{27}H_{31}NO_2Cl$. $H_2O$ requires C, 71.26; H, 6.86; N, 3.08%). m/z (ESI) (M$^+$, 400, 100%). $δ_H$ (CD$_3$OD) 1.05–1.85 (5H, m), 3.7 (2H, d, J 9.0 Hz), 4.45–4.52 (3H, m), 4.7 (1H, m), 5.19 (1H, dd, J 3.01, 6.0 Hz), 5.3 (1H, dd, J 3.0, 9.0 Hz), 5.9–6.1 (1H, m), 6.7–6.82 (3H, m), 7.1–7.39 (5H, m), 7.82 (2H, d, J 6.0 Hz) and 8.6 (2H, d, J 6.0 Hz).

INTERMEDIATE 7
4-{2-(R)-|3-Cyclopentyloxy-4-hydroxy-5-prop-3-enylphenyl|-2-phenyl}ethylpyridine hydrochloride Intermediate 6 (2.2 g, 5.51 mmol) was heated in a silicon oil bath at 230° C. for 2 h under nitrogen. The crude product was subjected to chromatography (SiO$_2$: MeOH—CH$_2$Cl$_2$, 5:95) to give the free base (1.41 g) as a yellow gum.

A small amount of the free base was treated with ethereal HCl to give the title compound as an off-white solid. m/z (ESI) (M+H, 400, 50%) (Found C, 71.57; H, 6.58; N, 3.00. $C_{27}H_{30}NO_2Cl$ requires C, 71.42; H, 6.66; N, 3.08%). $δ_H$ (CD$_3$OD) 1.5–1.98 (5H, m), 3.3 (2H, dd, J 3.0, 6.0 Hz), 3.68 (2H, dd, J 3.0, 6.0 Hz), 3.7 (2H, dd, J 3.0, 6.0 Hz), 4.32–4.45 (1H, m), 4.78 (1H,m), 4.9 (2H, dd, J 3.0, 9.0 Hz under HOD), 5.8–6.0 (1H, m), 6.6 (2H, dd, J 3.0, 30 Hz), 7.1–7.4 (5H, m), 7.81 (2H, d, J 3.0 Hz) and 8.6 (2H, d, J 3.0 Hz).

EXAMPLE 1 a) 4-|2-(5Cyclopentyloxy-2-iodo-4-methoxyphenyl)ethyl| pyridine

Silver triflate (2.57 g, 10.0 mmol) was added to a solution of Intermediate 4 (3.00 g, 10.0 mmol) in CHCl$_3$ (100 ml) at RT. A solution of iodine (2.54 g, 10.0 mmol) in CHCl$_3$ (100 ml) was added dropwise and the mixture allowed to stir for a further 1 h at RT. Sodium thiosulphate solution (100 ml) was added and the organic layer separated and combined with a CH$_2$Cl$_2$ portion (50 ml). The extract was dried (MgSO$_4$) and concentrated in vacuo. The residue was subjected to chromatography (SiO$_2$; Et$_2$O) to afford the title compound (3.89 g) as a pale yellow solid; $δ_H$ (CDCl$_3$) 1.4–1.9 (8H, br m, (CH$_2$)$_4$), 2.8–3.0 (4H, m, CH$_2$CH$_2$ pyridine), 3.81 (3H, s, OMe), 4.60 (1H, br m, OCH), 6.55 (1H, s, ArH meta to methoxy), 7.12 (2H, dd, J 4.5, 1.5 Hz, pyridine H$_3$, H$_5$), 7.22 (1H, s, ArH ortho to methoxy), and 8.50 (2H, dd, J 4.5, 1.5 Hz, pyridine H$_2$, H$_6$).

The following compound was prepared in a manner similar to the compound of Example 1a):

b) (R)-4-|2-(3-Cyclopentyloxy-6-iodo-4-methoxyphenyl)-2-phenylethyl|pyridine

From (R)-(+)-4-|2-(3-cyclopentyloxy-4-methoxyphenyl)-2-phenylethyl| pyridine (made as described in International Patent Specification No. WO 94/14742) (1.82 g, 4.88 mmol) in CHCl$_3$ (50 ml)m, silver triflate (1.26 g, 4.88 mmol) and iodine (1.24 g, 4.88 mmol). Chromatography (SiO$_2$:EtOAc) afforded the title compound (2.2 g) as a colourless gum. (Found C, 59.23; H, 5.32; N, 2.67. $C_{23}H_{26}NO_2I$ requires C, 60.13; H, 5.25; N, 2.81) $δ_H$ (CDCl$_3$) 1.5–1.9 (8H, m,CH$_2$)$_4$), 3.25 (1H, d, J 5 Hz, CH$_2$pyridine), 3.27 (1H, d, J 5 Hz, CH$_2$ pyridine), 3.74 (3H, s, OCH$_3$), 4.6–4.7 (1H, m, OCH), 4.64 (1H, t, J 8 Hz, CH phenyl), 6.74 (1H, s, C$_6$H$_2$), 7.01 (2H, d, J 5 Hz, H$_3$, H$_5$ pyridine), 7.24 (1H, s, C$_6$H$_2$), 7.25–7.4 (5H, m, C$_6$H$_5$), and 8.39 (2H, d, J 5 Hz, H$_2$, H$_6$ pyridine). m/z 500 (M$^+$, 100%), 406 (25) and 212 (14).

EXAMPLE 2
4-|2-(5-Cyclopentyloxy-4-methoxy-2-phenyl)ethyl| pyridine hydrochloride A solution of the compound of Example 1 (1.06 g, 2.5 mmol) in dioxane (10 ml) was added to a solution of tetrakis (triphenylphosphine)palladium (0.144 g, 0.125 mmol) in dioxane (20 ml) and the mixture stirred at RT for 0.5 h. Sodium carbonate solution (2M, 3.25 ml) and phenylboronic acid (0.305 g, 2.5 mmol) were then added and the mixture heated to reflux for 16 h. The cooled reaction mixture was poured into sodium hydrogen carbonate solution (20 ml) and extracted with CH$_2$Cl$_2$ (2×25 ml). The extract was dried (MgSO$_4$), concentrated in vacuo, and the residue subjected to chromatography (SiO$_2$; Et$_2$O) to afford the title compound free base.

The base was dissolved in Et$_2$O (20 ml) and treated with ethanolic HCl to afford the title compound (320 mg) as a pale yellow solid m.p. 179°–180° C.; $\delta_H$ (CDCl$_3$) 1.5–2.0 (8H, br m, (CH$_2$)$_4$), 2.6–2.7 (2H, m, CH$_2$CH$_2$), 2.89–2.9 (2H, m, CH$_2$CH$_2$), 3.80 (3H, s, OMe), 4.74 (1H, br m, OCH), 6.69 (1H, s, ArH ortho to alkoxy), 6.72 (1H, s, ArH ortho to alkoxy), 6.80 (2H, dd, J 4.5, 1.5 Hz, pyridine H$_3$, H$_5$), 7.2–7.5 (5H, m, C$_6$H$_5$), and 8.37 (2H, dd , J 4.5, 1.5 Hz, pyridine H$_2$, H$_6$); m/z (EI) 373 (M$^+$, 12%) 305 (17), 182 (18), 181 (100), 153 (28), 152 (22), 94 (17), 93 (46), and 69 (23).

EXAMPLE 3

(E)- and (Z)-isomers of 4-{2-|5-Cyclopentyloxy-4-methoxy-2-(2-phenylethenyl)phenyl|-ethyl}pyridine A mixture of the compound of Example 1 (1.27 g, 3.0 mmol), styrene (417 mg, 4.0 mmol), Et$_3$N (404 mg, 4.0 mmol), palladium (II) acetate (34 mg, 0.15 mmol), and tri-O-tolylphosphine (41 mg, 0.5 mmol) in acetonitrile (5 ml) was heated in a bomb at 140° C. for 24 h. The cooled reaction mixture was poured into sodium hydrogen carbonate solution (10 ml) and extracted with CH$_2$Cl$_2$ (2×25 ml). The extract was dried (MgSO$_4$), concentrated in vacuo, and the residue subjected to chromatography (SiO$_2$; Et$_2$O) to afford the title compound (1.05 g) as a cream solid m.p. 91°–94° C. $\delta_H$ (CDCl$_3$) 1.5–1.7 and 1.75–1.95 (8H, m, (CH$_2$)$_4$), 2.8–3.1 (4H, m, (CH$_2$)$_2$ pyridine), 3.90 (3H, s, OMe), 4.60–4.75 (1H, m, OCH), 6.51 (1H, s, ArH), 6.6–7.5 (8H, m, ArH+(CH)$_2$+C$_6$H$_5$), 7.07 (2H, d, J 7.5 Hz, H$_3$, H$_5$ pyridine), and 8.47 (2H, d, J 7.5 Hz, H$_2$, H$_6$ pyridine).

EXAMPLE 4

4-{2-(R)-|3-Cyclopentyloxy-4-methoxy-5-prop-3-enylphenyl|-2-phenyl}ethylpyridine To a stirred solution of Intermediate 7 (243 mg) in dry THF-DMF (8 ml; 3:1) at RT was added potassium tert-butoxide (90 mg). After 20 min, iodomethane (0.042 ml) was added and the solution stirred a further 40 min, then quenched with H$_2$O. The reaction mixture was partitioned between H$_2$O-EtOAc and the aqueous phase extracted with EtOAc. The combined organic phase was dried (MgSO$_4$) then evaporated. Chromatography (SiO$_2$; EtOAc-hexane, 30–50%) afforded the title compound (0.167 g) as a yellow oil. Found (C, 80.43; H, 7.52; N, 3.55. C$_{28}$H$_{31}$NO$_2$ requires C, 81.32; H, 7.56; N, 3.36%). $\delta_H$ (CDCl$_3$) 1.55–1.8 (8H, br m), 3.3 (4H, dd, J 6.0 Hz), 3.61 (3H, s), 4.13 (1H, t, J 9.0 Hz), 4.58 (1 H, s), 4.92–5.08 (2H, m), 5.82–5.97 (1H, m), 6.6 (2H, dd, J 3.0, 6.0 Hz), 6.92 (2H, d, J 6.0 Hz), 7.15–7.3 (5H, m), 8.4 (2H, d, J 6.0 Hz). m/z (ESI) 414 (M$^+$H 414, 100%).

FORMULATION EXAMPLES

The compounds of the invention may be formulated for pharmaceutical use in a number of forms using any suitable excipients. Thus, for example, for oral use the compounds of the invention such as the compounds of the Examples may be formulated as a solid dosage form, by mixing an appropriate weight of compound (for example 50 mg) with maize starch (50–99% w/w), anhydrous colloidal silica (0–10% w/w) and organic or inorganic acid (up to 1% w/w), to fill capsules of an appropriate size, e.g. white opaque hard gelatine capsules size 3. If desired the same mixture may be compressed into tablets.

The activity and selectivity of compounds according to the invention was demonstrated in the following tests. In these tests the abbreviation FMLP represents the peptide N-formyl-met-leu-phe.
Isolated Enzyme The potency and selectivity of the compounds of the invention was determined using distinct PDE isoenzymes as follows:

i. PDE I, rabbit heart ii. PDE II, rabbit heart iii. PDE II, rabbit heart, Jurkat cells iv. PDE IV, HL60 cells, rabbit brain, rabbit kidney and human recombinant PDE IV v. PDE V, rabbit lung, guinea pig lung A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (*Beavo and Reifsnyder*, 1990, *TIPS*, 11, 150). These recombinant enzymes, particularly the human eosinophil recombinant PDE IV, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50 mM 2-||tris (hydroxymethyl)methyl|amino|-1-ethane-sulphonic acid (TES) —NaOH buffer (pH 7.5), 10 mM MgCl$_2$, 0.1 μM |$^3$H|-cAMP and vehicle or various concentrations of the test compounds. The reaction was initiated by addition of enzyme and conducted at 30° C. for between 5 to 30 mins. The reaction was terminated by addition of 50 μl 2% trifluoroacetic acid containing |$^{14}$C]-5'AMP for determining recovery of the product. An aliquot of the sample was then applied to a column of neutral alumina and the |$^3$H|-cAMP eluted with 10 ml 0.1 TES—NaOH buffer (pH 8). The |$^3$H|-5'-AMP product was eluted with 2 ml 2M NaOH into a scintillation vial containing 10 ml of scintillation cocktail. Recovery of |$^3$H|-5'AMP was determined using the |$^{14}$C|-5'AMP and all assays were conducted in the linear range of the reaction.

Compounds according to the invention such as the most potent compounds of the Examples herein cause a concentration-dependent inhibition of recombinant PDE IV at 0.1–1000 nM with little or no activity against PDE I, II III or V at concentrations up to 100 μM.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 1 μM.

3. Suppression of Leukocyte Function

Compounds of the invention were investigated for their effects on superoxide generation, chemotaxis and adhesion of neutrophils and eosinophils. Isolated leukocytes

We claim:

1. A compound of formula (1)

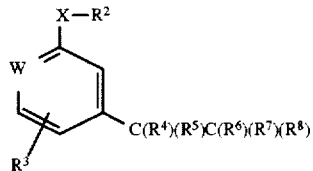

wherein:

=W— is =C(Y)—;

Y is halogen or an alkyl or —XR$^a$ group;

X is —O—, —S(O)$_m$— or —N(R$^a$)—, where m is zero or an integer 1 or 2;

R$^a$ is hydrogen or an optionally substituted alkyl group;

R$^2$ is an optionally substituted cycloalkyl or cycloalkenyl group;

R$^3$ is R$^{13}$ or —L$^1$R$^{13}$, where R$^{13}$ is an optionally substituted straight or branched chain C$_{2-6}$alkenyl group or an optionally substituted C$_{6-12}$ monocyclic or bicyclic aryl group and L$^1$ is an optionally substituted straight or branched chain C$_{1-6}$alkylene, C$_{2-6}$alkenylene or C$_{2-6}$alkynylene group;

R$^4$ is a hydrogen atom or a group —(CH$_2$)$_n$Ar where Ar is an optionally substituted monocyclic aryl group and n is zero or an integer 1, 2 or 3;

R$^5$ is hydrogen;

R$^6$ is an optionally substituted 2-, 3- or 4-pyridyl group; and each of R$^7$ and R$^8$ is independently hydrogen or an optionally substituted straight or branched alkyl group;

or a pharmaceutically acceptable salt, hydrate, solvate or N-oxide thereof.

2. A compound according to claim 1 wherein R$^2$ is an optionally substituted cyclopentyl group.

3. A compound according to claim 1 wherein R$^3$ is R$^{13}$.

4. A compound according to claim 3 wherein R$^3$ is an optionally substituted straight or branched chain C$_{2-6}$alkenyl group.

5. A compound according to claim 4 wherein R$^3$ is an optionally substituted propenyl group.

6. A compound according to claim 3 wherein R$^3$ is an optionally substituted C$_{6-12}$ monocyclic or bicyclic aryl group.

7. A compound according to claim 6 wherein R$^3$ is an optionally substituted 1- or 2-naphthyl group.

8. A compound according to claim 2 wherein R$^3$ is —L$^1$R$^{13}$.

9. A compound according to claim 8 wherein L$^1$ is an optionally substituted straight or branched chain C$_{1-6}$alkylene or C$_{2-6}$alkenylene group and R$^{13}$ is an optionally substituted phenyl group.

10. A compound according to claim 9 wherein R$^3$ is phenylethyl or phenylethenyl.

11. A compound according to claim 1 wherein R$^6$ is an optionally substituted 4-pyridyl group.

12. A compound of formula (2)

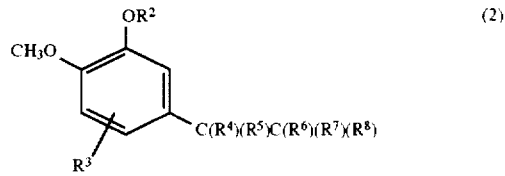

wherein:

R$^2$ is an optionally substituted cycloalkyl group;

R$^3$ is an optionally substituted straight or branched chain C$_{2-6}$alkenyl group, an optionally substituted Ar group, an optionally substituted ArC$_{1-3}$alkyl group or an optionally substituted ArC$_{1-3}$alkenyl group, where Ar is a C$_{6-12}$ monocyclic or bicyclic aryl group;

R$^4$ is a hydrogen atom or a group —(CH$_2$)$_n$Ar' where Ar' is an optionally substituted monocyclic aryl group and n is zero or an integer 1, 2 or 3;

R$^5$ is hydrogen;

R$^6$ is an optionally substituted 2-, 3- or 4-pyridyl group; and each of R$^7$ and R$^8$ is hydrogen;

or a pharmaceutically acceptable salt, hydrate, solvate or N-oxide thereof.

13. A compound according to claim 12 which is 4-{2-[3-Cyclopentyloxy-4-methoxy-5-prop-3-enylphenyl]-2-phenyl}ethylpyridine; and the pharmaceutically acceptable salts, solvates, hydrates, and N-oxides thereof.

14. A compound which is selected from the group consisting of:

4-{2-[3-Cyclopentyloxy-4-methoxy-5-prop-3-enylphenyl]-2-phenyl}ethylpyridine;

4-{2-[5-Cyclopentyloxy-4-methoxy-2-(2-phenylethenyl)phenyl]ethyl}pyridine;

4-{2-[5-Cyclopentyloxy-4-methoxy-2-(2-phenylethyl)phenyl]ethyl}pyridine;

4-{2-[5-Cyclopentyloxy-4-methoxy-2-(1-naphthyl)phenyl]ethyl}pyridine;

4-{2-[5-Cyclopentyloxy-4-methoxy-2-(2-naphthyl)phenyl]ethyl}pyridine;

or the isomers and enantiomers thereof, and the pharmaceutically acceptable salts, hydrates, solvates, and N-oxides thereof.

15. A pharmaceutical composition comprising, in combination with one or more pharmaceutically acceptable carriers, excipients or diluents, an effective amount of a compound according to claim 12.

16. A compound according to claim 13 which is 4-{2-(R)-[3-Cyclopentyloxy-4-methoxy-5-prop-3-enylphenyl]-2-phenyl}ethylpyridine; and the pharmaceutically acceptable salts, solvates, hydrates, and N-oxides thereof.

17. A pharmaceutical composition comprising, in combination with one or more pharmaceutically acceptable carriers, excipients or diluents, an effective amount of a compound according to claim 1.

18. A pharmaceutical composition comprising, in combination with one or more pharmaceutically acceptable carriers, excipients or diluents, an effective amount of a compound according to claim 16.

* * * * *